(12) United States Patent
Paquin et al.

(10) Patent No.: US 6,858,646 B2
(45) Date of Patent: Feb. 22, 2005

(54) NEUROPROTECTIVE COMPOSITION AND USES THEREOF

(75) Inventors: Joanne Paquin, Montréal (CA); Mircea-Alexandru Mateescu, Montréal (CA); Éric De Grandpré, Joliette (CA)

(73) Assignee: Universite du Quebec a Montreal, Montreal (CA)

( * ) Notice: Subject to any disclaimer, the term of this patent is extended or adjusted under 35 U.S.C. 154(b) by 117 days.

(21) Appl. No.: 10/021,735

(22) Filed: Nov. 5, 2001

(65) Prior Publication Data

US 2002/0128316 A1 Sep. 12, 2002

Related U.S. Application Data (63) Continuation of application No. PCT/CA00/00523, filed on May 5, 2000.

(30) Foreign Application Priority Data

May 5, 1999 (CA) .............................................. 2270795

(51) Int. Cl.⁷ ...................... A61K 31/355; A61K 31/19; A61K 31/20; A61K 31/07; A61K 31/015
(52) U.S. Cl. ...................... 514/458; 514/557; 514/558; 514/725; 514/763
(58) Field of Search ................................. 514/557, 558, 514/560, 458, 725, 763

(56) References Cited

U.S. PATENT DOCUMENTS

| 5,395,822 A | 3/1995 | Izumi et al. ................... 514/3 |
| 5,652,274 A | 7/1997 | Martin ....................... 514/724 |

FOREIGN PATENT DOCUMENTS

| DE | 34 42 725 | 5/1996 | .......... A61K/31/70 |

OTHER PUBLICATIONS

M.S. Gokhale et al. "A Mixture of Antioxidants and Fatty Acids Improves the Viability of Cultured Rat Hepatocytes Untreated with Doxorubicin", XP–000995528, Toxicology in Vitro (1997) 753–759.

Alain Martin, "The Use of Antioxidants in Healing", XP 000578697, Dermatol Surg 1996;22:146–160.

*Primary Examiner*—Raymond J. Henley, III
(74) *Attorney, Agent, or Firm*—Barry H. Jacobsen; Evan J. Federman (57) ABSTRACT

A neuroprotective composition for protecting neuronal cells against oxidative stress and methods for using and preparing the same. More particularly, the neuroprotective composition of the invention comprises a mixture of pyruvate, antioxidant, and lipid(s) such as fatty acids. The neuroprotective composition could be used for the treatment of brain trauma, brain or cerebrovascular ischemia, neurodegenerative diseases, poisoning of neuronal cells, the diminution of drugs side effects and for preservation of neuronal grafts.

19 Claims, 6 Drawing Sheets

FIG. 9    Hydrogen peroxide concentration (mM)

FIG. 10    Hydrogen peroxide concentration (mM)

FIG. 11    Hydrogen peroxide concentration (mM)

FIG. 12    Hydrogen peroxide concentration (mM)

NEUROPROTECTIVE COMPOSITION AND USES THEREOF

This is a continuation of international application Serial No. PCT/CA00/00523, filed May 5, 2000, the entire disclosure of which is hereby incorporated by reference.

BACKGROUND OF THE INVENTION

1. Field of the Invention

The present invention relates to the use of an amphiphilic antoxidant composition as a neuroprotective agent and to methods for using and preparing the same. More particularly, the present invention pertains to the use of a formulation of pyruvate, antioxidant, and lipid(s) such as fatty acids for protecting neurons against oxidative stress.

2. Description of the Prior Art

Reactive oxygen species (ROS) have been implicated in the development of many heart and brain dysfunctions. Ischemia/reperfusion insults to these organs are among the leading causes of mortality in America. These insults are caused by complete or partial local occlusions of heart and brain vasculature, by heart stroke or attack, and by cerebral attacks and trauma to the brain. In addition, ROS are involved in artherosclerotc lesions, in the evolution of various neurodegenerative diseases, and are also produced in association to epileptic episodes, in inflammation, in the mechanisms of action of various neurotoxicants, or as side-effects of drugs.

Until now, no ideal therapeutic agent is known to protect neuronal cells against oxidant species associated with various types of oxidative stress. It would therefore be highly desirable to have such neuroprotective agent.

TRIAD is combination of pyruvate, antioxidant and fatty acids. This composition has been patented in 1997 in the U.S. as a therapeutic wound healing compositions (U.S. Pat. No. 5,652,274). Many related U.S. patents have also been issued for covering the uses of TRIAD in antkeratolytic compositions (U.S. Pat. No. 5,641,814); in anti-fungal compositions (U.S. Pat. No. 5,663,208); in acne healing compositions (U.S. Pat. No. 5,646,190); in anti-inflammatory compositions (U.S. Pat. No. 5,648,380); in dermatological compositions (U.S. Pat. No. 5,602,183); in sunscreen compositions (U.S. Pat. No. 5,674,912); in antihistamine compositions (U.S. Pat. No. 5,614,561); in cytoprotective compositions (U.S. Pat. No. 5,633,285); in wound healing composition affixed to razor cartridges (U.S. Pat. No. 5,682, 302); and in regenerating compositions (EP 0 573 465 B1). However, none of these patents discloses or suggests the use of TRIAD as neuroprotective agent.

In view of the above, it is clear that there is a need for an amphiphilic antioxidant composition comprising pyruvate, antioxidant, and lipid(s) such as fatty acids to protect neuronal cells against oxidant species.

The purpose of this invention is to fulfil this need along with other needs that will be apparent to those skilled in the art upon reading the following specification.

SUMMARY OF THE INVENTION

The present invention relates to a neuroprotective composition and more particularly to an amphiphilic antioxidative composition and its uses.

According to an aspect of the invention, the neuroprotective composition comprises a therapeutically effective amount of a mixture of pyruvate, antioxidant(s), and lipid(s) such as fatty acids. These components are present in an amount that have a synergistic protective effect on neuronal cells.

In a preferred embodiment, lipids consist of a mixture of saturated and unsaturated fatty acids selected from the group consisting of monogylcerides, digylcerides, trigylcerides, free fatty acids, and mixtures thereof.

Preferably, pyruvate is selected from the group consisting of pyruvic acid, pharmaceutically acceptable salts of pyruvic acid, prodrugs of pyruvic acid, and mixtures thereof.

Preferably, also the antioxidant is selected from lipid-soluble antioxidants, and more preferably the antioxidant is selected from the group consisting of Vitamin A, carotene, Vitamin E, pharmaceutically acceptable salts thereof, and mixtures thereof.

According to an other aspect of the invention, the neuroprotectve composition is used as such or as an active agent in the preparation of a medication for the treatment of neuronal cells. Such treatments include the treatment brain trauma, brain or cerebrovascular ischemia, neurodegenerative diseases, poisoning of neuronal cells, the diminution of drugs side effects and for preservation of neuronal grafts.

According to an other aspect of the invention, the invention provides a method for treating neuronal oxidative stress related condition, the method comprising administrating to a patient in need thereof a therapeutically effective amount of an antioxidative composition comprising pyruvate, at least one antioxidant and at least one lipid.

Alternatively, the invention also provides a method for treating neuronal oxidative stress related condition comprising: a) administrating to a patient in need thereof, a therapeutically effective amount of an antioxidative composition comprising pyruvate and at least one antioxidant; and b) providing, into the blood circulation of this patient, at least one lipid having a synergistic therapeutic effect on neuronal cells in combination with said antioxidative composition. The lipid(s) could be provided to the patient by increasing its lipidic blood level ratio through its diet. Examples of neuronal oxidative stress related condition include a neurodegenerative disease, such as amyotrophic lateral sclerosis, Alzheimer's disease, Parkinson's disease Huntington's disease, etc, brain trauma, brain or cerebrovascular ischemia, neuronal cells poisoning, side effects caused by a drug and the preservation of neuronal grafts.

According to an other aspect of the invention it is provided a method for preparing a neuroprotective composition, the method comprising the steps of:

a) providing a therapeutically effective amount of: i) pyruvate, ii) at least one antoxidant; and iii) at least one lipid;

b) mixing together the components i), ii) and iii) of step a) in a physiological buffered saline solution to obtain a pharmaceutically acceptable homologous suspension; and optionally c) centrifuging or filtering the homologous suspension obtained in step b).

The buffered saline solution may comprises sodium, potassium, magnesium and calcium ions at physiological concentrations and if necessary, an emulsifier.

An advantage of the present invention is that it provides effective means for preventing the loss of viability or functions of neuronal cells in conditions of oxidative stress. It can also protect a neuronal cell from a toxic substance, stabilizes the cellular membrane of a neuronal cell and/or helps in the normalization of neuronal cellular functions.

Other objects and advantages of the present invention will be apparent upon reading the following non-restrictive description of several preferred embodiments made with reference to the accompanying drawings.

DETAILED DESCRIPTION OF THE INVENTION

As stated hereinbefore the present invention relates to the use of an amphiphilic antioxidant compositions as neuroprotective agent. As disclosed herein, a composition comprising sodium pyruvate, antioxidant and lipid(s) such as fatty acids have neuroprotective actions against oxidative stress.

Unless defined otherwise, all technical and scientific terms used herein have the same meaning as commonly understood by one ordinary skilled in the art to which this invention belongs.

As used herein, the term "neuroprotectve agent" or "neuroprotectve composition" refers to any compound (or to any mixture of compounds) that protects a neuronal cell from a toxic substance, stabilizes the cell membrane of a neuronal cell and/or helps in the normalization of neuronal cell functions. A "neuroprotective agent" thereby prevents the loss of viability or functions of neuronal cells in stressing conditions.

Therefore, the term "neuroprotecton" as used herein refers to the capacity of a neuroprotective agent to maintain or stimulate the capacity of neuronal cells to maintain or recover their neuronal functions even in pathological or harmful conditions such as oxidative stress conditions.

As stated out above, the neuroprotective composition of the invention comprises a mixture of (a) pyruvate, (b) at least one antioxidant, and (c) at least one lipid such as fatty acids, preferably a mixture of saturated and unsaturated fatty acids. According to the invention, these three components have a synergistic beneficial effect on neuronal cells, i.e. their combined effect is greater than the sum of their individual effects.

The pyruvate in the present invention may be selected from the group consisting of pyruvic acid, pharmaceutically acceptable salts of pyruvic acid, prodrugs of pyruvic acid, and mixtures thereof. In general, the pharmaceutically acceptable salts of pyruvic acid may be alkali salts and alkaline earth salts. Preferably, the pyruvate is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, α-ketoglutaric acid, and mixtures thereof. More preferably, the pyruvate is selected from the group of salts consisting of sodium pyruvate, potassium pyruvate, magnesium pyruvate, calcium pyruvate, zinc pyruvate, manganese pyruvate, and the like, and mixtures thereof. Most preferably, the pyruvate is sodium pyruvate.

The amount of pyruvate present in the neuroprotective composition of the present invention is a therapeutically effective amount. A therapeutically effective amount of pyruvate is that amount of pyruvate necessary for the neuroprotective composition to prevent and/or reduce injury of a neuronal mammalian cell. The exact amount of pyruvate will vary according to factors such as the type of condition being treated as well as the other ingredients in the composition. Typically, the amount of pyruvate should vary from about 0.01 mM to about 100 mM. In a preferred embodiment, pyruvate is present in the composition of the neuroprotective extracellular medium in an amount from about 0.1 mM to about 30 mM, preferably from about 0.5 mM to about 10 mM. In the most preferred embodiment, the neuroprotective composition comprises about 10 mM of sodium pyruvate.

Antioxidants, including vitamin antioxidants, are substances which inhibit oxidation or suppress reactions promoted by oxygen, oxygen free radicals (OFR), oxygen reactive species (ORS) including peroxides. Antioxidants, especially lipid-soluble antioxidants, can be absorbed into the cell membrane to neutralize oxygen radicals and thereby protect the membrane. The antioxidants useful in the present invention are preferably vitamin antioxidants that may be selected from the group consisting of all forms of Vitamin A including retinal and 3,4-didehydroretinal, all forms of carotene such as alpha-carotene, β-carotene, gamma-carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopyran-6-ol), β-tocopherol, gamma-tocopherol, delta-tocopherol, tocoquinone, tocotrienol, and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof. Preferably, the antioxidant is selected from the group of lipid-soluble antioxidants consisting of Vitamin A, β-carotene, Vitamin E, Vitamin E acetate, and mixtures thereof. More preferably, the antioxidant is Vitamin E or Vitamin E acetate. Most preferably, the antioxidant is Vitamin E acetate. Analogues of Vitamin E such as Trolox®, a compound which is more hydrosoluble than natural forms of Vitamin E and which could reach intracellular sites more rapidly, could also be used according to the present invention.

The amount of antioxidant present in the neuroprotective composition of the present invention is a therapeutically effective amount. A therapeutically effective amount of antioxidant is that amount of antioxidant necessary for the neuroprotective composition to prevent and/or reduce injury of a neuronal mammalian cell. The exact amount of antioxidant will vary according to factors such as the type of condition being treated as well as the other ingredients in the composition. Typically, the amount of antioxidant should vary from about 0.01 unit/ml to about 10 unit/ml. In a preferred embodiment, vitamin E antioxidant is present in the composition of the neuroprotective extracellular medium in an amount from about 0.01 unit/ml to about 10 unit/ml, preferably from about 0.05 to about 5 unit/ml. In the most preferred embodiment, the neuroprotective composition comprises about 1 unit of antioxidant (α-tocopherol type VI in oil) per ml of neuroprotective composition.

As it is well known, lipids are esters or carboxylic acid compounds found in animal and vegetable fats and oils. The composition may comprises a single type of lipid or various types of different lipids. Preferably lipids are in the form of a mixture of saturated and unsaturated fatty acids. However, other types of lipids could be used such as glycolipids and phospholipids (e.g. lecithin). Lipid(s) or mixture thereof are selected among those lipids required for the stabilization and/or repair of the membrane of neuronal mammalian cells. These lipids may be derived from animal or vegetables. In a preferred embodiment, selected lipids are in the form of mono-, di-, or triglycerides, or free fatty acids, or mixtures thereof, which are readily available for the stabilizauon or repair of the membrane of neuronal mammalian cells. Artificial lipids which are soluble in organic solvents and are of a structural type which includes fatty acids and their esters, cholesterols, cholesteryls esters could also be used according to the present invention.

In a more preferred embodiment, the saturated and unsaturated fatty acids are those deriving from egg yolk. According to the use of the neuroprotective compositions of the invention, replacing egg yolk as a source of fatty acids by chemical preparations of unsaturated, polyunsaturated and/or saturated fatty acids compatible with, and in proportions similar to those found in cell membranes may be advantageous or reveal necessary to insure a controllable quality of preparations.

The amount of lipid(s) such as fatty acids present in the neuroprotective composition of the present invention is a therapeutically effective amount. A therapeutically effective amount of fatty acids for instance is that amount of fatty acids necessary for the neuroprotective composition to prevent and/or reduce injury of a neuronal mammalian cells. The exact amount of lipid(s) or fatty acids will vary according to factors such as the type of condition being treated as well as the other ingredients in the composition. Typically, the amount of lipid(s) or fatty acids should vary from about 0.001% v/v to about 1% v/v. In a preferred embodiment, fatty acids are present in the neuroprotective composition in an amount from about 0.001% v/v to about 0.3% v/v, preferably from about 0.005% v/v to about 0.1% v/v. In the most preferred embodiment, the neuroprotective composition comprises about 0.1% v/v of fresh egg yolk.

As the lipidic blood level of an individual is normally about 0.5–0.6% of the total serum volume, the lipidic portion could be omitted from the neuroprotective composition of the invention. It could be possible to provide into the blood circulation of this individual at least one lipid having a synergistic therapeutic effect on neuronal cells with the others component of the antioxidative neuroprotective composition of the invention. For instance, selected lipid(s) could be provided by increasing the lipidic blood level ratio of this individual through the diet. Lipids which could have a synergistic therapeutic effect without being harmful to a patient could be selected from the group consisting of phospholipids, glycolipids, fatty acids, and mixture thereof.

Further agents can be joint to the neuroprotective composition of the invention. For examples various antioxidants may complete the action of europrotective composition such as:

ceruloplasmin or its analogues since it can scavenge $.O_2^-$ radicals and has a ferroxidase activity which oxidizes $Fe^{2+}$ to $Fe^{3+}$;

metal chelators/scavengers (e.g. desferrioxamine [Desferal®], a small substance capable to scavenge $Fe^{3+}$ and other metal ions);

proteins or their fragments that can bind metal ions such as ferritin or transferrin which both bind $Fe^{3+}$;

scavengers of .OH (hydroxyl) or NO (nitric oxide) radicals (e.g. mannitol).

small scavengers of $.O_2^-$ (superoxide), .OH (hydroxyl) or NO (nitric oxide) radicals (e.g. acetyl salicylic acid, scavenger of $.O_2^-$; mannitol or captopril, scavengers of .OH) or molecules that inhibit the generation of these radicals (e.g. arginine derivatives, inhibitors of nitric oxide synthase which produce NO);

proteins or their fragments that scavenge oxygen free radicals and can assist the protective action of ceruloplasmin (e.g. superoxide dismutase which dismutate $.O_2^-$; hemoglobin which traps NO); and proteins or their fragments that can scavenge $H_2O_2$ (hydrogen peroxide) in cases where they may exert a more potent or durable protective action than pyruvate (e.g. catalase, glutathion peroxidase).

The composition of the invention may also comprises modulators of brain functions such as neurotransmitters, neuropeptides, hormones, trophic factors, or analogs of these substances that act by binding to brain receptors (e.g. DOPA in Parkinson's disease).

Further to the therapeutic agents, the neuroprotective composition of the invention may also contain preserving agents, solubilizing agents, stabilizing agents, wetting agents, emulsifiers, sweeteners, colorants, odorants, salts, buffers, or coating agents. For preparing the neuroprotective composition, methods well known in the art may be used.

The method of preparation of the neuroprotective compositions of the invention is very simple as it consists simply in the mixing of components in a buffered saline solution in order to get a homogenous suspension. Suitable saline solution comprises sodium, potassium, magnesium and calcium ions at physiological concentrations, has an osmotic pressure varying from 280 to 340 mosmol, and a pH varying from 7.2 to 7.4. Depending of the amount and of type of lipid(s) which is used, the saline may also comprises an emulsifier. Preferably, the buffered saline solution is selected from the group consisting of modified Krebs-Henseleit buffer (KH) and phosphate buffer saline (PBS), both at pH 7.4. The homogenous suspension obtained can further be centrifuged and/or filtered to reduce its viscosity and/or eliminated non-soluble particles.

Obviously, this simple method can be modified according to the use of the neuroprotective composition. In the example found hereunder, a genuine preparation was used. Centrifuged and/or filtered preparations could also have been used. However, it is important to note that modifications in the modality of preparation can influence the resulting effects of the neuroprotective composition. For example, varying the pH of the composition (or buffer) can slightly modify the ionization state of carboxylic functions of pyruvate and thus alter its solubility and/or reaction with $H_2O_2$, while the dialysis of the composition would reduce the amount of pyruvate in the final preparation, unless it is done before addition of pyruvate. A person skilled in the art will know how to adapt the preparation of the neuroprotectve composition of the invention according to its desired use in specific conditions in order to obtain positive desired effects.

The neuroprotective composition of the invention could be suitable to treat diseases and pathological conditions such as brain trauma and diseases which were shown to involve oxidative stress conditions such as amyotrophic lateral sclerosis and neurodegenerative Parkinson's, Alzheimer's and Huntington's diseases. These neuroprotective compositions could also be involved in the treatment of poisoning or diminution of side effects of various drugs (such as chemotherapeutic and immunosuppressive drugs) to the brain and/or to neuronal cells. Indeed, deleterious action of various toxicants and drugs is exerted via production of ROS.

The neuroprotective composition of the invention has potential applications in both fast (in minutes; especially due to the pyruvate) and long term treatments (hours and days; due to the antioxidant and lipid(s) such as fatty acids). The amount to be administered is a therapeutically effective amount. A therapeutically effective amount of a neuroprotective composition is that amount necessary for protecting a neuronal cell from the loss of viability or function induced by a toxic substance, stabilizing the cell membrane of neuronal cells and/or helping in the normalization of neuronal cell functions. Suitable dosages will vary, depending upon factors such as the type and the amount of each of the components in the composition, the desired effect (fast or long term), the disease or disorder to be treated, the route of administration and the age and weight of the individual to be treated.

The neuroprotective composition of the invention and/or more complex pharmaceutical compositions comprising the same may be given orally (per os) in the form of tablets, capsules, powders, syrups, etc. since all their components are absorbable by the gastrointestinal tract. Others administration ways can also be considered (rectal and vaginal capsules or nasally by means of a spray). They may also be formulated as creams or ointments for topical administration. They may also be given parenterally, for example intravenously, intramuscularly or sub-cutaneously by injection or by infusion. Intravenous administration can be a way for fast answer in various clinical conditions (e.g. ischemic brain, brain trauma, stroke and heart attacks, post-surgery treatments, etc). Obviously, the neuroprotective compositions of the invention may be administered alone or as part of a more complex pharmaceutical composition according to the desired use and route of administration. Anyhow, for preparing such compositions, methods well known in the art may be used.

As it will now be demonstrated by way of an example hereinafter, the composition of the invention possesses a strong neuroprotective activity i.e. the capacity to maintain the viability and functions of neurons at their normal level or to induce a fast recovery to the normal level, even in pathological or harmful conditions such as oxidative stress conditions. These conditions can occur at post-ischemia reperfusion of the brain associated with an attack to brain vasculature, cerebral trauma or a heart stroke/attack, in various neurodegenerative diseases, in epilepsy, following an exposure to neurotoxicants, or as side-effects of drugs and inflammation. Although any methods and materials similar or equivalent to those described herein can be used in the practice or testing of the present invention, the preferred methods and materials are described.

EXAMPLE

Neuroprotective Actions of TRIAD Against Oxidative Stress

Abstract

This work shows that TRIAD, a combination of sodium pyruvate, vitamin E and egg yolk fatty acids, has an antioxidant protective action on cultured P19 neurons exposed to oxidative stress. Oxidative stress was induced by incubation with prooxidant systems that generate major reactive oxygen species produced by ischemia-reperfusion of the brain in vivo, namely 1) xanthine/xanthine oxidase system to produce $.O_2^-$ superoxide radicals and $H_2O_2$, 2) $H_2O_2$ it self, and 3) $H_2O_2$ in the presence of $Fe^{2+}$ to produce .OH hydroxyl radicals. TRIAD-induced resistance to injury caused by oxidative stress was assessed by measurement of cell viability. TRIAD concentrations less than 3× permitted to achieve complete protection of neurons. Optimal concentrations of TRIAD with neurons exposed to peroxide-based systems were directly related to the oxidant power of the systems as measured by oxidation of N,N-diethyl-p-phenylenediamine. However, higher concentrations of TRIAD than those predicted from in vitro analyses were required to protect neurons against oxidative stress. In addition, the results also show that the respective contribution of pyruvate and of fatty acids+vitamin E combination may differ between prooxidant systems and between in vitro or cell culture situations. These results indicate that TRIAD components have different mechanisms of action and that these mechanisms are further modulated by cell metabolism. Generally, in our experimental models, pyruvate was a major contributor of the antioxidant action of TRIAD and its effect was increased by fatty acids and vitamin E in some cases in an additive manner and in other cases synergistically.

Abbreviations

DPD: N,N-diethyl-p-phenylenediamine; KH: Krebs-Henseleit; $LD_{50}$: lethal dose 50 or dose that causes 50% mortality; PBS: phosphate buffer saline; OFR: oxygen free radical; ROS: reactive oxygen species; XA: xanthine; XAO: xanthine oxidase, SOD: superoxide dismutase; CAT: catalase; GP: glutathion (GSH)-peroxidase.

1. Introduction 1.1 Oxidative Stress and Antioxidant Defenses in Normal and Pathophysiological Heart and Brain Reactive oxygen species (ROS) including hydrogen peroxide, oxygen free radicals (OFR) such as superoxide and hydroxyl radicals, and their derivatives are generated by normal cellular metabolism but are potent cellular toxicants when they are produced in excess and thus cause an oxidative stress to cells (LeBel and Bondy, 1991; Gutteridge, 1994; Chan, 1996). The organism has several strategies to maintain ROS-induced damage at low levels: a) to eliminate ROS (e.g. SOD, CAT and GP enzymes shown in FIG. 1), b) to scavenge ROS by trapping them (e.g. ascorbic acid) or by breaking their propagation (e.g. vitamin E), c) to sequester iron or other metals in non- or low reactive forms, and d) to repair molecular damages (Gutteridge, 1994).

ROS have been implicated in the development of many heart and brain dysfunctions (Takemura et al., 1994; Chan, 1996; Maiese, 1998) and ischemia/reperfusion insults to these organs are among the leading causes of mortality in America (Takemura et al., 1994; Chan, 1996; Maiese, 1998). These insults are caused by complete or partial local occlusions of vasculature and by trauma to heart and brain. ROS as those found in ischemia-reperfusion events are also involved in the evolution of several neurodegenerative diseases or produced in brain following an exaggerated activity of this organ (e.g. epilepsy).

Various pathways generating superoxide radical ($.O_2^-$) and other ROS—also known as reactive oxygen intermediates (ROI)—have been identified, such as: activation of polymorphonuclear leukocytes, autoxidation of catecholamines, reactions of xanthine oxidase and NADPH oxidase, or metabolism of arachidonic acid. The harmful effects of superoxide radical and its by products are dramatically increased in the presence of transition metals. The ferrous ($Fe^{2+}$) ion generated by the Haber-Weiss reaction catalyses the formation of the highly aggressive hydroxyl (.OH) radical, via Fenton reaction. The OFR concentration at reperfusion is higher than during ischemia. OFR may contribute to reperfusion injury by interacting with membrane polyunsaturated fatty acids (PUFA) and generating lipid peroxides which increase membrane permeability and alter ionic homeostasis. Inhibition of free radical accumulation with OFR scavengers, antioxidant enzymes, and spin-trap agents was shown to reduce the severity of damages to brain. However, the benefits of these treatments gradually vanish with time, especially during long-term utilization in neurodegenerative diseases, or are lessen by the apparition of adverse secondary effects. Therefore, the identification of other therapeutics agents still remains highly desirable.

1.2 Aspects on TRIAD and Its Therapeutic Role

As stated herein before, TRIAD is a combination of pyruvate, antioxidant and fatty acids for which many uses have been patented. Preferably, TRIAD comprises sodium pyruvate, vitamin E and egg yolk. Although this combination is also known under the name of CRT (Cellular Resuscitation Therapy), the current denomination of TRIAD is use throughout this document.

These three agents were shown to act synergistically to ameliorate wound healing (Martin, 1996; Sheridan et al., 1997) and to reduce oxidative damage to keratinocytes and monocytes exposed to ultraviolet light (Martin, 1996) or to hepatocytes treated with doxorubicin (Gokhale et al., 1997). The presumed respective role of each agent of the antioxidant combination is a) for pyruvate, to bind stochiometrically to $H_2O_2$, b) for vitamin E, to interrupt the propagation of lipid peroxidation, and c) for egg yolk, to provide a balanced mix of fresh unsaturated and saturated fatty acids which will help in membrane repair (Martin, 1996).

1.3 Presentation of the Study

The goal of this study was to determine if TRIAD has an antioxidant protective action on cultured P19 neurons exposed to oxidative stress. The choice of this model is related to the fact that the P19 cell line is establishing itself as a flexible model of neurons of central nervous system. Oxidative stress was induced by incubation with prooxidant systems that generate major ROS produced by ischemia-reperfusion in vivo. Prooxidant systems used are: i) XA/XAO system to produce $.O_2^-$ and $H_2O_2$ ii) $H_2O_2$ it self, and iii) $H_2O_2$ in the presence of $Fe^{2+}$ to produce .OH. Resistance of neurons to injury induced by oxidative stress was assessed by measurement of cell viability. In all cases, different concentrations of TRIAD were tested in order to determine those that permitted to achieve a complete protection and also tested the contribution of TRIAD components to the overall protection. In addition, when applicable, the antioxidant properties of TRIAD in vitro were measured in order to understand some aspects of the protection afforded by this mix in live models.

2. Materials and Methods

Materials

Vitamin E (α-ocopherol type VI in oil), sodium pyruvate, ethylenediamine tetraacetic acid (EDTA), N,N-diethyl-p-phenylenediamine (DPD), and xanthine (XA) were purchased from Sigma Chem. Co. Xanthine oxidase (XAO) was from Boehringer Mannheim. Neurobasal®, L-glutamine and B27 supplement were from Gibco-BRL. Alamar Blue was purchased from Medicorp (Montreal, Quebec). Fresh egg yolk was used as the source of fatty acids. The other current chemicals were reagent grade (from Sigma Chem. Co., St-Louis) and were used without further purification.

Methods 2.1 Preparation of TRIAD

The 133 TRIAD concentration was prepared as per Gokhale et al. (1997) and contained 0.1% v/v fresh egg yolk, 1 unit/ml vitamin E (α-tocopherol type VI in oil) and 10 mM sodium pyruvate. Stock 5× (5 fold) or 10× (10 fold) concentration of TRIAD was freshly prepared before each experiment by carefully mixing the three agents to get a homogenous suspension. TRIAD mixtures were made in phosphate buffer saline (PBS; 136 mM NaCl, 2.7 mM KCl, 1.5 mM $KH_2PO_4$ and 8 mM $Na_2HPO_4$, pH 7.4). Pyruvate was soluble in and egg yolk miscible with this saline physiological buffer. Aseptically drawn egg yolk and vitamin E suspension (vitamin E in oil combined to 70% ethanol in a 2.5:1 ratio) were added at the desired final concentrations to a 100 mM stock pyruvate solution prepared in PBS and filter-sterilized on 0.22 μm.

Although not tested with neuronal cells, a modified preparation of TRIAD was shown to be effective to protect isolated hearts. Modification of TRIAD preparations was as follows: 5× or 10× genuine preparations were centrifuged at 15000×g for 20 min, at 4° C., and the resulting supernatants (S1) filtered on Whatman paper filter #54. The final filtered supernatant was named TRIAD (S2) and used to perfuse hearts. The different concentrations of TRIAD (S2) preparation were obtained by subsequent dilution with Krebs-Henseleit physiological saline buffer (i.e. TRIAD (S2) 1× was obtained by 10 fold dilution of stock TRIAD (S2) 1× preparation).

2.2 Culture and Neuronal Differentiation of P19 Cells

Culture and neuronal differentiation of P19 embryonal carcinoma cells were done according to the procedures of Jeannotte et al. (1997) with the following modifications for microscale adaptation of cultures to 96-well plates: cell aggregates obtained at day 4 of the treatment of P19 cells with retinoic acid were trypsinized with 0.025% trypsin-1 mM EDTA in PBS and subjected to mechanical passages to obtain individual cells which were seeded in gelatin-precoated microwells at a density of $0.7–1\times10^5$ cells per well. The newly seeded cells (neurons) were cultured in supplemented Neurobasal medium (Neurobasal® containing 0.5 mM L-glutamine and 0.5% B27 supplement) until exposure to oxidative conditions at day 7. Because this defined serum-free medium sustains growth of P19 neurons (Yao et al., 1995) but discourages the proliferation of fibroblasts, another cell derivative of the differentiation of P19 cells with retinoic acid (McBurney, 1993; Jeannotte et al., 1997), the cell populations in microwells were composed mostly of neurons ($\leq 95\%$).

2.3 Exposure of P19 Neurons to Prooxidant Systems

The prooxidant systems tested with P19 neurons were XA/XAO, $H_2O_2$, and $H_2O_2/Fe^{+2}$. Before neurons were exposed to either one of these systems, they were carefully washed with PBS and then incubated at 37° C., in an atmosphere of 95% ambient air and 5% $CO_2$, and in the specific conditions of each system, as follows: i) from 0 to 90 min in the presence of PBS containing 500 $\mu M$ XA and 50 mU/ml XAO, with the enzyme added last to start the reaction; ii) for 30 min in the presence of PBS containing 0 to 10 mM $H_2O_2$ with peroxide added last; and iii) for 30 min in the presence of PBS containing 0 to 10 mM $H_2O_2$ plus 50 $\mu M$ $FeCl_2$, with peroxide added last. Conditions were initially taken from Cini et al. (1994) for XA/XAO, from Desagher et al. (1996) for $H_2O_2$, and from Takemura et al. (1994) for $H_2O_2/Fe^{+2}$ systems respectively, and adapted to produce dose- or time-dependent cell mortality in P19 neurons. The first studies done with the $H_2O_2/Fe^{2+}$ system included the addition of 500 $\mu M$ ascorbic acid; however, since responses of P19 neurons were similar whether or not ascorbic acid was present, this vitamin was omitted in subsequent experiments.

When TRIAD or its components were tested for their antioxidant action, they were administered to cells just prior the addition of XAO or $H_2O_2$. After incubation of cells under oxidative conditions, the prooxidant medium was removed and replaced with 200 $\mu l$ of supplemented Neurobasal-minus AO (Neurobasal® containing L-glutamine and the B27-minus AO supplement). B27-minus AO is a version of B27 supplement sold by Gibco-BRL from which normally present antioxidants (AO= vitamin E, catalase, SOD and GSH) have been removed. Cells were incubated in this Neurobasal-minus AO medium for 16 h, at 37° C., 5% $CO_2$, and for a further 7 h in the same medium but in the presence of Alamar Blue for viability measurement.

Another protocol was also tested for XA/XAO system to generate a milder oxidative stress. In this new protocol, P19 neurons were exposed during 40 min to 250 $\mu M$ XA and varying concentrations of XAO (0 to 20 mU/mL) in PBS. At end of stress, PBS was changed for Neurobasal-minus AO medium and cells were incubated for 7 h, readily in the presence of Alamar Blue, for viability measurement.

2.4 Cell Viability Assay

Fifteen (15) $\mu l$ Alamar Blue was added to the culture medium of each well (200 $\mu l$) and incubation resumed for 7 h at 37° C., 5% $CO_2$. A 180-$\mu l$ aliquot of each culture medium was read by fluorescence using a wavelength of 544 nm for excitation and of 590 nm for emission; fluorescence increases upon reduction of the dye by metabolic activity of viable cells. Fluorescence determinations were done with a fluorimeter adapted to read microplates. Viability is reported as %, comparing the fluorescence units obtained for cells exposed to oxidative conditions to those of control (non-exposed) cells.

2.5 In Vitro Antioxidant Capacity

Oxidation of N,N-diethyl-p-phenylenediamine (DPD) by a prooxidant system was used as a general reporter of the amount of ROS generated by that system (Anonymous, 1985; Chahine et al., 1991). Antioxidant capacity of preparations of TRIAD (or of its components) was defined as the ability to inhibit the oxidation of DPD by prooxidants.

To estimate the antioxidant capacity of TRIAD preparations in the prooxidant conditions used with P19 neurons, DPD was added to a final concentration of 32 mM to 200 $\mu l$ of each prooxidant system described above (see section 2.4) and incubated for the times tested with the cells. At the end of incubation, the amount of oxidized DPD was determined at 560 nm using a spectrophotometer adapted to microscale measurement.

3. Results

The P19 embryonal carcinoma cell line is establishing its place as a versatile cell model for neurons of central nervous system (McBurney, 1993; Yao et al., 1994; Finley et al., 1996; Parnas and Linial, 1997; Jeannotte et al., 1997). These cells differentiate into neurons, astrocytes and fibroblast-like cells following induction with retinoic acid, and their neuronal derivatives mature into functional neurons. Indeed, P19-derived neurons express a variety of neuron-specific proteins, acquire cell polarity of neurons, form synapses, synthesize and release neurotransmitters and neuropeptides, and their membranes respond to electrophysiological stimuli (McBurney, 1993; Finley et al., 1996; Parnas and Linial, 1997; Jeannotte et al., 1997). The P19 system presents several advantages over other neuronal models for screening tests using cultured cells: i) P19 neurons like primary neurons are highly differentiated (in contrast, neuroblastoma cells often used as neuronal models are poorly differentiated), ii) acquisition of P19 neurons does not depend on the sacrifice of animals, and iii) although P19 neurons are post-mitotic and therefore do not divide as do neuroblastoma cells, they can be obtained in large quantities since P19 stem cells propagate at high rates. Considering that they resemble primary neurons and can be easily and reproductively obtained, we thus used P19 neurons to study the neuroprotective action of TRIAD.

Legends to the Figures

Figure 1:
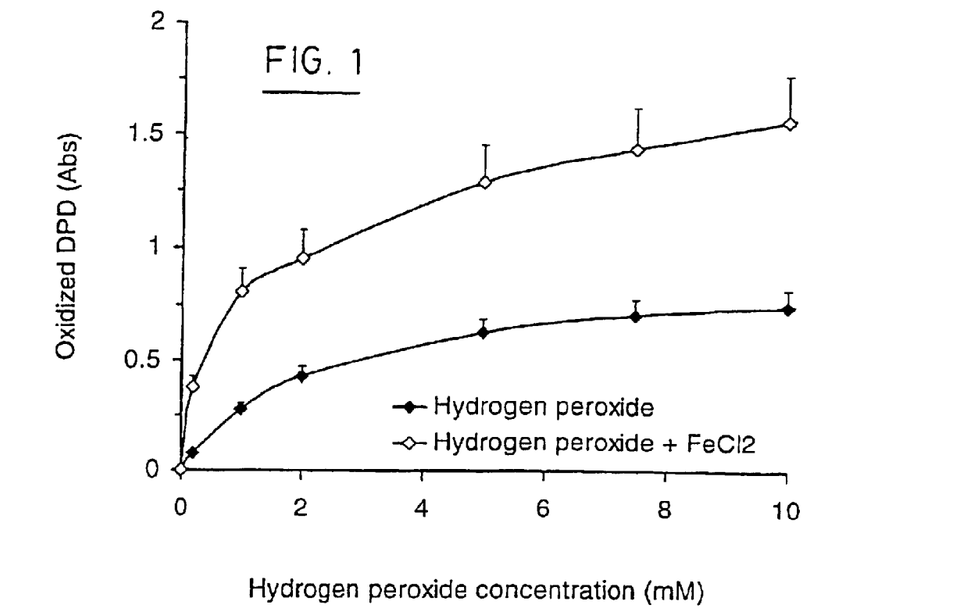
FIG. 1 is a graph showing the in vitro ROS production by peroxide-based prooxidant systems used with P19 neurons.

FIG. 1. In vitro ROS production by peroxide-based prooxidant systems used with P19 neurons. The relative amount of ROS produced by $H_2O_2$ and $H_2O_2/Fe^{2+}$ systems in the conditions used with P19 neurons were measured spectrophotometrically, in absence of cells, by following oxidation of N,N-diethyl-p-phenylenediamine (DPD). The experiment was done twice, in triplicate determinations, and results are expressed as means±errors to the means. The $H_2O_2/Fe^{2+}$ system contained 50 $\mu M$ $FeCl_2$; the addition of 500 $\mu M$ ascorbic acid to this system did not change the amount of oxidized DPD (not shown), indicating that iron ions were in a concentration sufficient to increase the oxidative stress induced by $H_2O_2$ alone.

Figure 2:
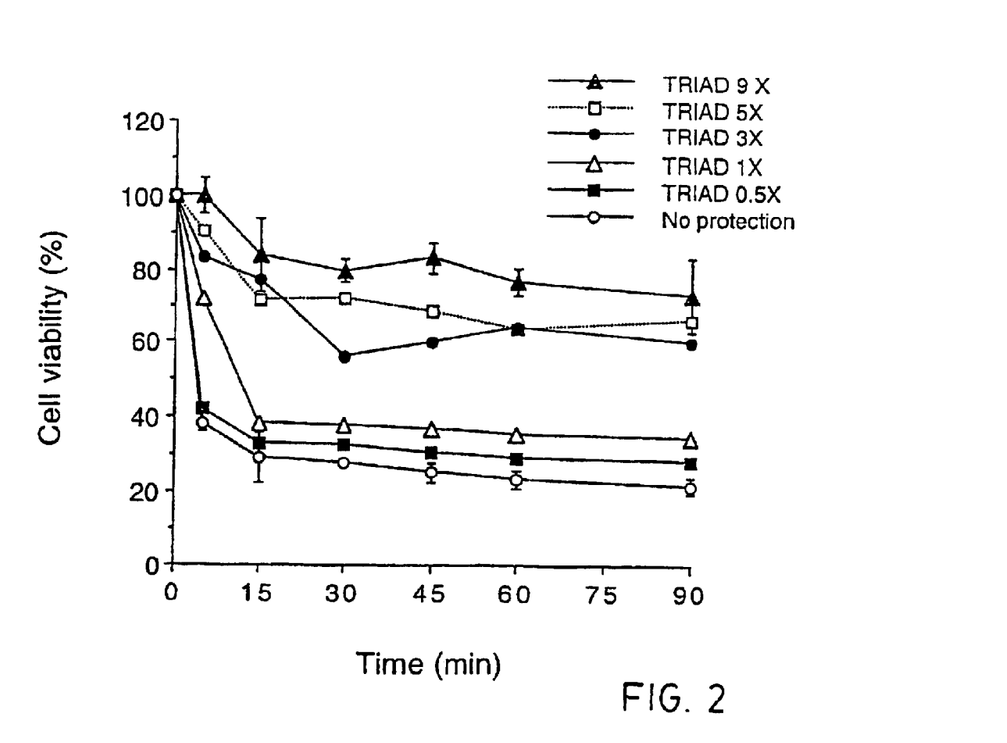
FIG. 2 is a graph showing the protection provided by TRIAD to P19 neurons exposed for different times to XA/XAO mediated oxidative stress.

FIG. 2. Protection provided by TRIAD to P19 neurons exposed for different times to XA/XAO mediated oxidative stress. P19 neurons were exposed from 0 to 90 min to 500 $\mu M$ XA and 50 mU/mL XAO in the absence (No protection) or presence of different concentrations of TRIAD. At end of stress, cells were incubated for 16 h in a fresh provision of culture medium lacking XA, XAO and TRIAD. Afterward, Alamar Blue was added and cells were further incubated for 7 h for viability determination. Viability values are reported as percentages, with 100% corresponding to the response of P19 neurons not exposed to XA/XAO. The experiment was done once, in duplicate determinations, and results are expressed as means (±errors to the means). Error bars are similar for all curves although they are shown for two curves only, for the purpose of clarity.

Figure 3:
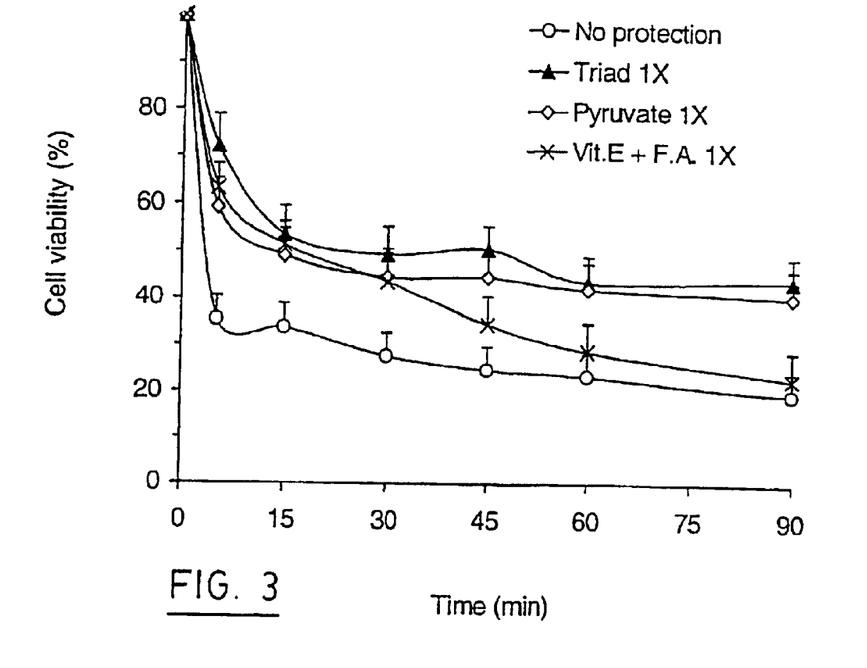
FIG. 3 is a graph showing the protection provided by TRIAD components to P19 neurons exposed for different times to XA/XAO mediated oxidative stress.

FIG. 3. Protection provided by TRIAD components to P19 neurons exposed for different times to XA/XAO mediated oxidative stress. Exposure to XA/XAO and viability measurement were done as indicated in the legend to FIG. 2. The experiment was done twice, in duplicate determinations, and results are expressed as means±errors to the means.Vit.E, vitamin E; F.A., fatty acids.

Figure 4:
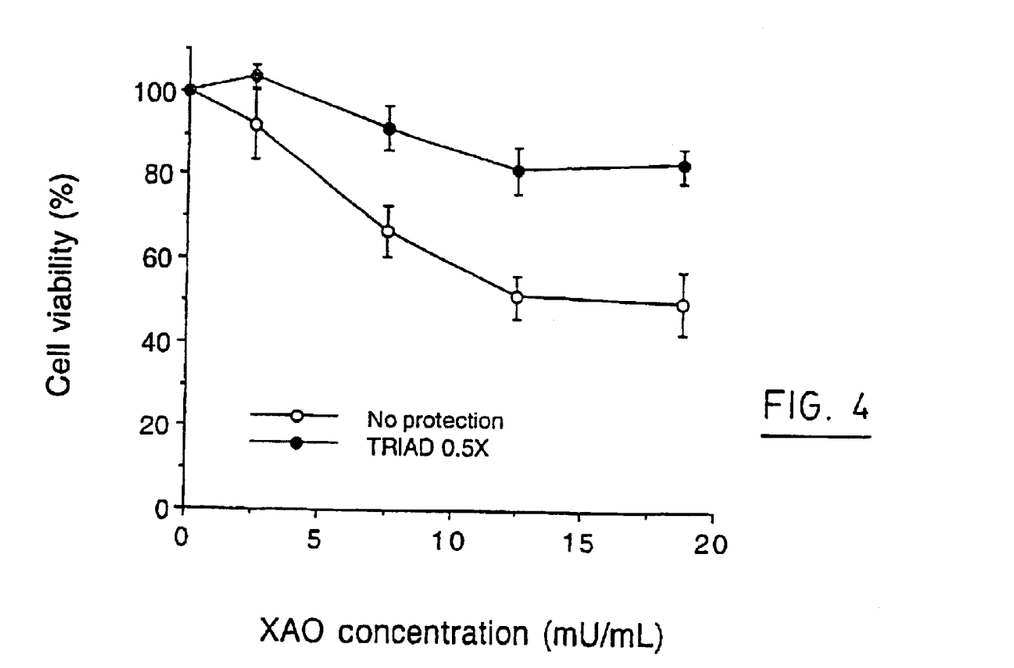
FIG. 4 is a graph showing the protection provided by TRIAD to P19 neurons exposed to oxidative stress mediated by different concentrations of XAO.

FIG. 4. Protection provided by TRIAD to P19 neurons exposed to oxidative stress mediated by different concentrations of XAO. P19 neurons were exposed for 40 min to 250 μM XA and different concentrations of XAO in the absence (No protection) or presence of 0.5×TRIAD. At end of stress, cells were incubated for 7 h in a fresh provision of culture medium lacking XA, XAO and TRIAD, but containing Alamar Blue for viability determination. Viability values are reported as percentages, with 100% corresponding to the response of P19 neurons not exposed to XA/XAO. The experiment was done twice, in triplicate determinations, and results are expressed as means±errors to the means.

Figure 5:
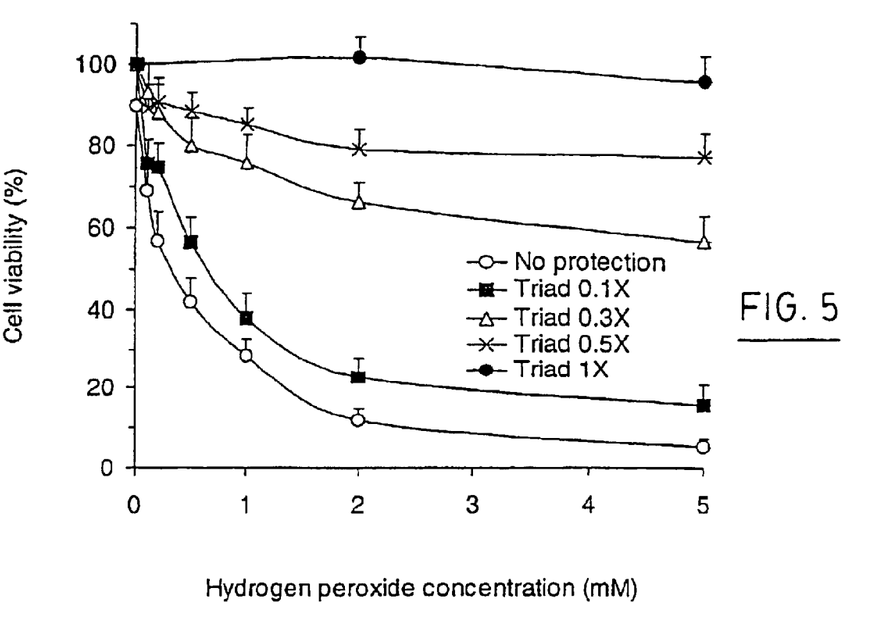
FIG. 5 is a graph showing the protection provided by TRIAD to P19 neurons exposed to hydrogen peroxide mediated oxidative stress.

FIG. 5. Protection provided by TRIAD to P19 neurons exposed to hydrogen peroxide mediated oxidative stress. P19 neurons were exposed during 30 min to different concentrations of $H_2O_2$ in the absence (control=no protection) or presence of different concentrations of TRIAD. At end of stress, cells were incubated for 16 h in a fresh provision of culture medium lacking $H_2O_2$ and TRIAD. Alamar Blue was then added and cells were further incubated for 7 h for viability determination. Viability values are reported as percentages, with 100% corresponding to the response of P19 neurons not exposed to $H_2O_2$. The experiment was done 5 times, in duplicate determinations, and results are expressed as means±S.D. Omission of the 16 h incubation period did not change the relative responses.

Figure 6:
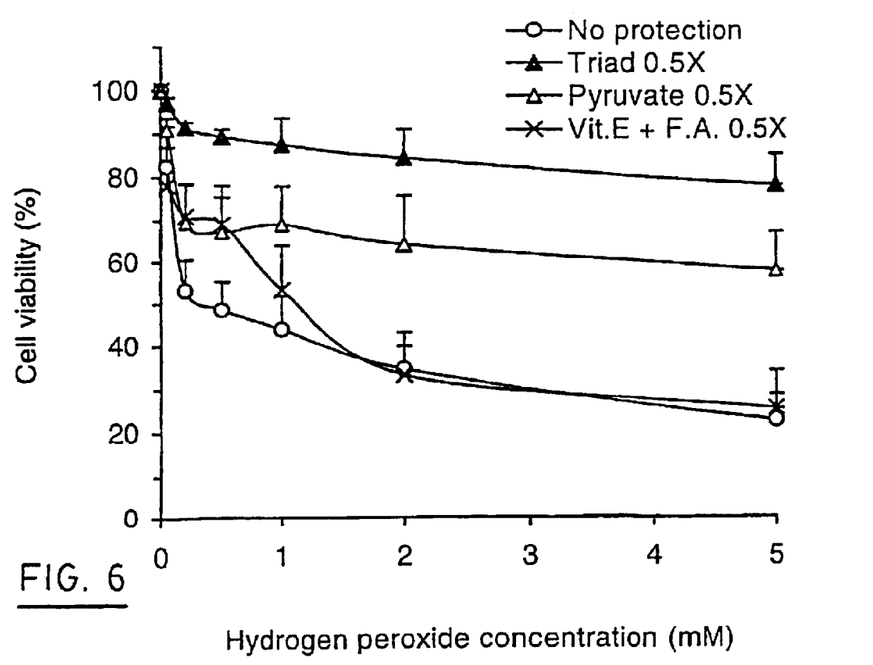
FIG. 6 is a graph showing the protection provided by TRIAD components to P19 neurons exposed to hydrogen peroxide mediated oxidative stress.

FIG. 6. Protection provided by TRIAD components to P19 neurons exposed to hydrogen peroxide mediated oxidative stress. Exposure to $H_2O_2$ and viability measurement were done as indicated in the legend to FIG. 5. The experiment was done four times, in triplicate determinations, and results are expressed as means±S.D. Vit.E, vitamin E; F.A., fatty acids.

Figure 7:
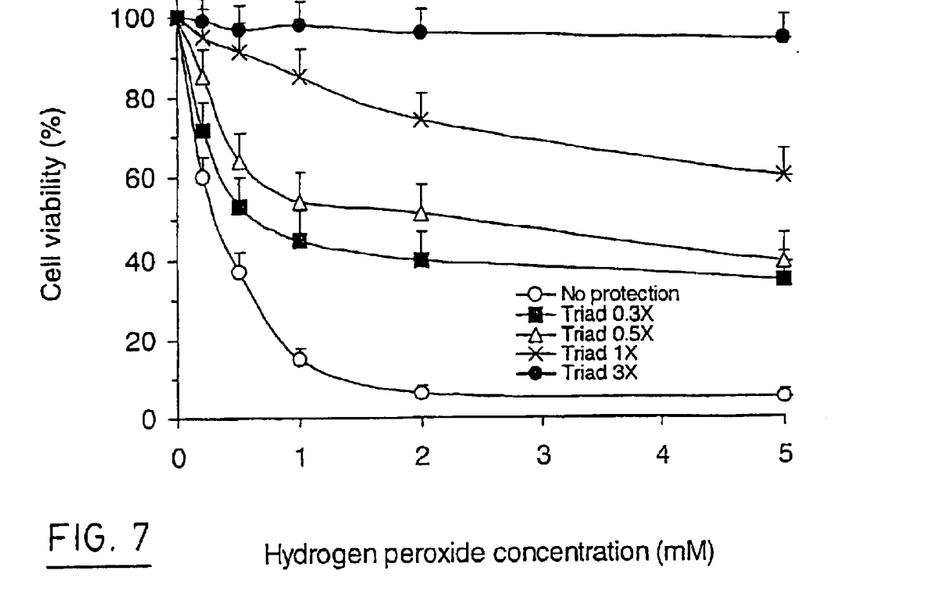
FIG. 7 is a graph showing the protection provided by TRIAD to P19 neurons exposed to $H_2O_2/Fe^{2+}$ prooxidant system.

FIG. 7. Protection provided by TRIAD to P19 neurons exposed to $H_2O_2/Fe^{2+}$ prooxidant system. Cell treatments were as described in the legend to FIG. 5 except that iron (50 μM $FeCl_2$) was present in the stress medium to generate hydroxyl radicals. Viability values are reported as percentages, with 100% corresponding to the response of P19 neurons not exposed to $H_2O_2/Fe^{2+}$. The experiment was done 3 times, in duplicate determinations, and results are expressed as means±S.D.

Figure 8:
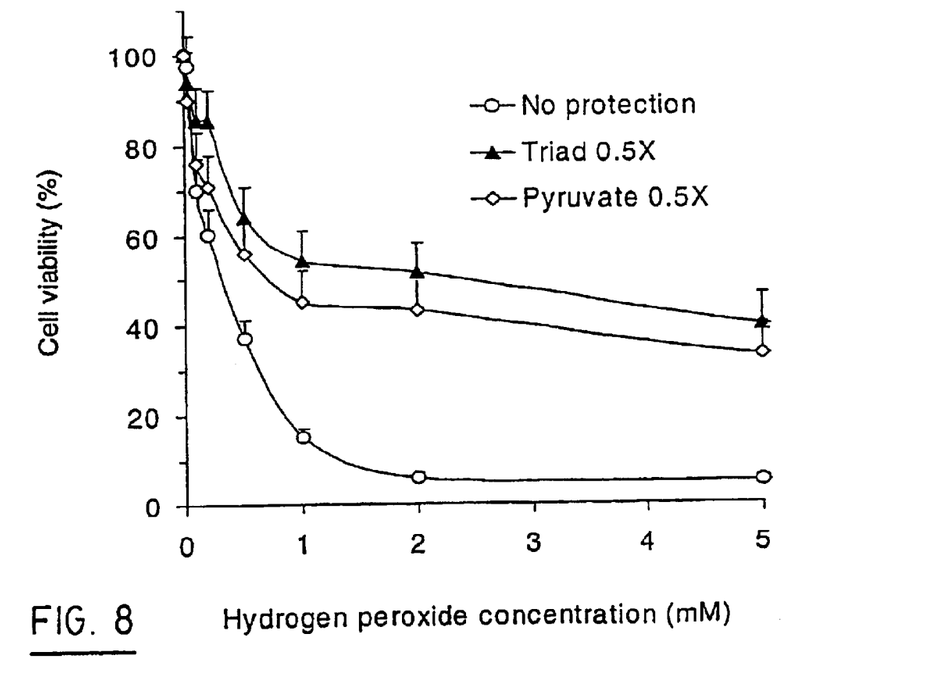
FIG. 8 is a graph showing the protection provided by TRIAD components to P19 neurons exposed to $H_2O_2/Fe^{2+}$ prooxidant system.

FIG. 8. Protection provided by TRIAD components to P19 neurons exposed to $H_2O_2/Fe^{2+}$ prooxidant system. Exposure to $H_2O_2/Fe^{2+}$ and viability measurement were done as indicated in the legend to FIG. 7. The experiment was done twice, in duplicate determinations, and results are expressed as means±errors to the means. Vitamin E+fatty acids did not protect in that system (not shown).

Figure 9:
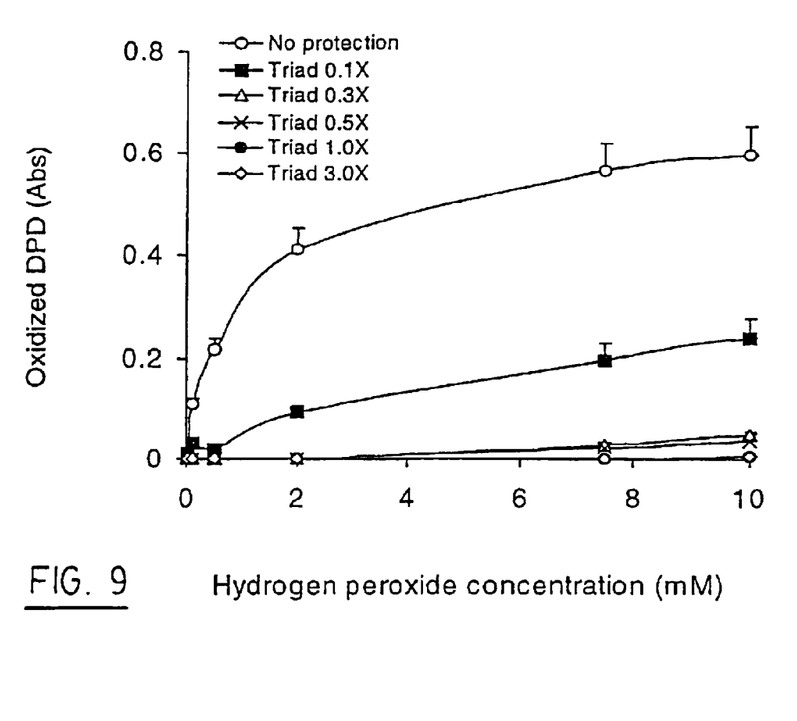
FIG. 9 is a graph showing the in vitro antioxidant capacity of TRIAD in the $H_2O_2$ prooxidant system used with P19 neurons.

FIG. 9. In vitro antioxidant capacity of TRIAD in the conditions of $H_2O_2$ prooxidant system used with P19 neurons. Effect of different concentrations of TRIAD on the oxidation of DPD induced by $H_2O_2$. The experiment was done 5 times, in duplicate determinations, and results are expressed as means±S.D.

Figure 10:
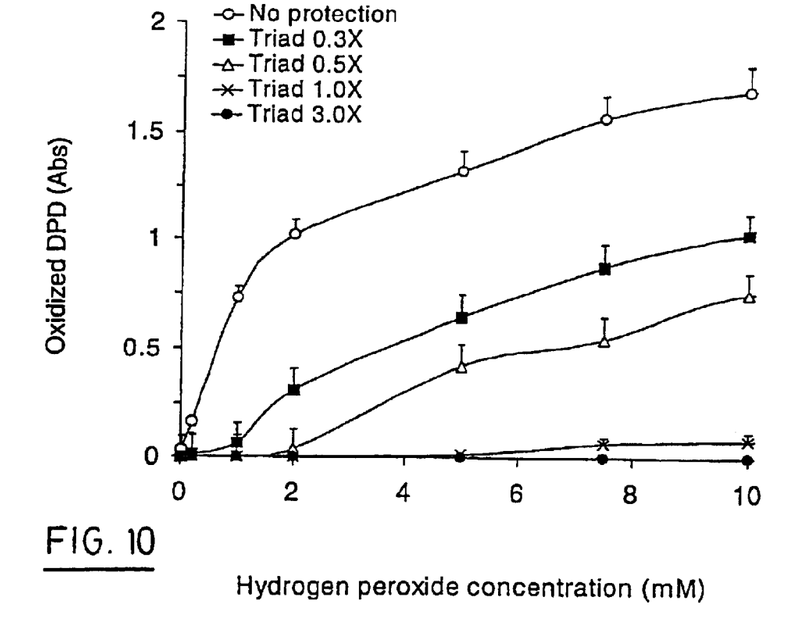
FIG. 10 is a graph showing the in vitro antioxidant capacity of TRIAD in the conditions of $H_2O_2/Fe^{2+}$ prooxidant system used with P19 neurons.

FIG. 10. In vitro antioxidant capacity of TRIAD in the conditions of $H_2O_2/Fe^{2+}$ prooxidant system used with P19 neurons. Effect of different concentrations of TRIAD on the oxidation of DPD induced by $H_2O_2/Fe^{2+}$. The experiment was done 7 times, in duplicate determinations, and results are expressed as means±S.D.

Figure 11:
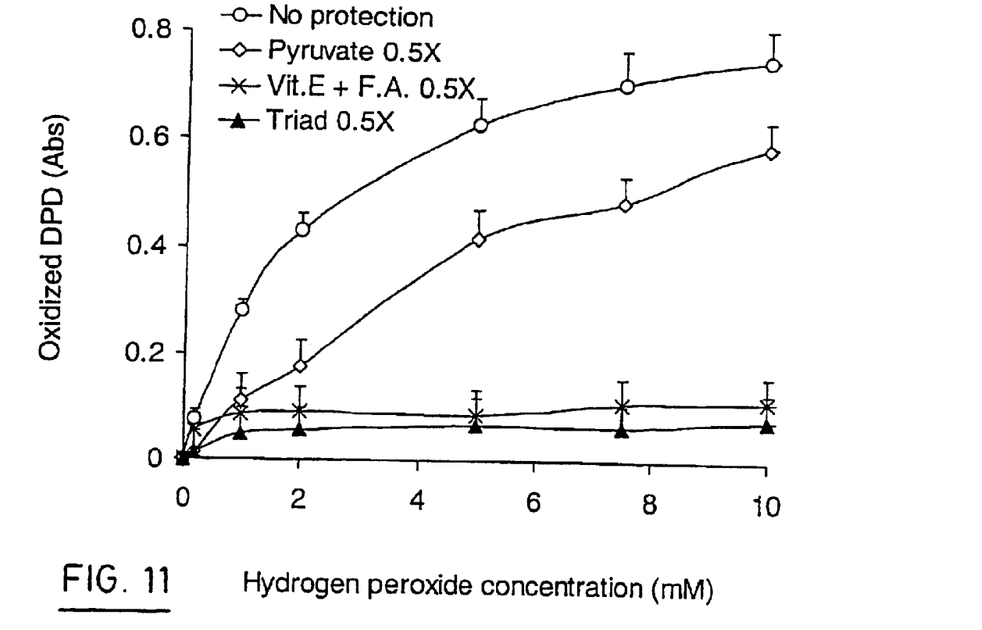
FIG. 11 is a graph showing the in vitro antioxidant capacity of TRIAD components in the conditions of $H_2O_2$ prooxidant system used with P19 neurons.

FIG. 11. In vitro antioxidant capacity of TRIAD components in the conditions of $H_2O_2$ prooxidant system used with P19 neurons. Effect of TRIAD components on the oxidation of DPD induced by $H_2O_2$. The experiment was done 4 times, in duplicate determinations, and results are expressed as means±S.D. Vit. E, vitamin E; F.A., fatty acids.

Figure 12:
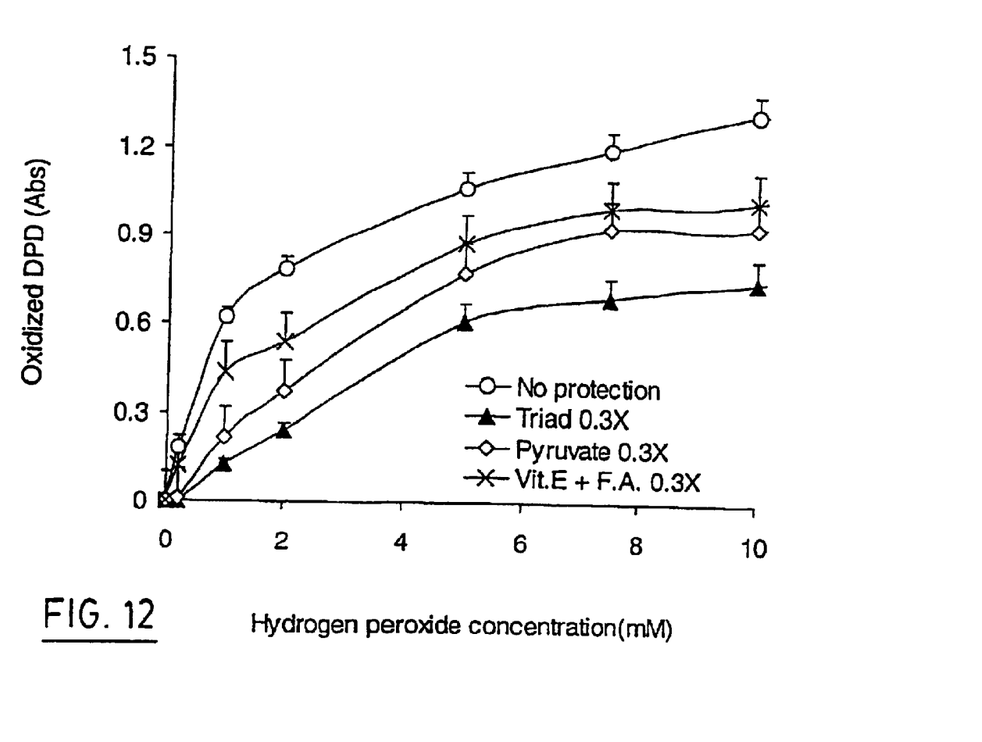
FIG. 12 is a graph showing the in vitro antioxidant capacity of TRIAD components in the conditions of $H_2O_2/Fe^{2+}$ prooxidant system used with P19 neurons.

FIG. 12. In vitro antioxidant capacity of TRIAD components in the conditions of $H_2O_2/Fe^{2+}$ prooxidant system used with P19 neurons. Effect of TRIAD components on the oxidation of DPD induced by $H_2O_2/Fe^{2+}$. The experiment was done 3 times, in duplicate determinations, and results are expressed as means±S.D. Vit. E, vitamin E; F.A., fatty acids.

3.1 In vitro Oxidant Capacity of Peroxide-based Prooxidant Systems Used with P19 Neurons Three prooxidant systems were used to induce oxidative stress in P19 neurons, namely XA/XAO, $H_2O_2$, and $H_2O_2/Fe^{+2}$. The relative oxidant capacity of the two peroxide-based system was determined by following oxidation of DPD in vitro. FIG. 1 shows that addition of $Fe^{+2}$ increased the oxidant power of $H_2O_2$. Comparison with the oxidant power of XA/XAO system could not be done since this system did not directly oxidize DPD. It is believed that addition of SOD enzyme to XA/XAO system in vitro would convert $.O_2^-$ radicals produced by the system to measurable proportionate amounts of $H_2O_2$ molecules.

3.2 Neuroprotection Afforded by TRIAD Against Oxidative Stress Induced by XA/XAO When exposed during 90 min to TRIAD in the absence of an oxidative stress, P19 neurons remained completely viable even for concentration 9× of the antioxidant mix (results not shown). Since genuine preparations of TRIAD were not toxic to these cells, they were used without further treatment (i.e. TRIAD and not TRIAD (S2) was used with P19 neurons). However, as explained hereinbefore (see section 2.1), the genuine preparations could have been centrifuged and the resulting supernatants filtered.

XA/XAO system was used to generate superoxide radicals $(.O_2^-)$ in addition to $H_2O_2$. When exposed to that system for different times, a large proportion of P19 neurons died after 5 min (FIG. 2, No protection). When TRIAD was present in the culture medium, it decreased cell mortality caused by the prooxidant conditions. Protection was concentration dependent and reached almost completion at concentration 9× of TRIAD (FIG. 2). The individual contribution of fatty acids, vitamin E and pyruvate to the protection provided by TRIAD against neuronal death caused by XA/XAO was also determined. A 1× concentration for TRIAD and its components was used instead of an optimal value of 9× in order to reveal the eventual synergistic effects, if any. FIG. 3 shows that pyruvate 1× protected only slightly less than TRIAD 1×. Fatty acids and vitamin E together protected similarly to pyruvate or TRIAD during the 30 first min of incubation with XA/XAO (FIG. 3). However, the protective effect fell off rapidly from 30 to 90 min while that of pyruvate remained stable (FIG 3). At 90 min of exposure, the summation of the protective effect separately shown by pyruvate and by fatty acids+vitamin E reproduced the protection provided by TRIAD itself (FIG. 3), indicating that fatty acids and vitamin E had an additive effect on pyruvate action.

It was realized that the pro-oxidant conditions used just above were probably very drastic since most neurons died after 5 min (FIGS. 2 and 3, No protection). According to the protocol used, cells were exposed to 500 μM XA and 50 mU/mL XAO. for up to 90 min, then incubated in fresh culture medium—not containing XA/XAO—for 16 h hours in the absence of AlamarBlue, and for a further 7 h in the presence of the dye. It was believed that any residual amount of XA/XAO left in the culture medium had time to continue to attack neurons, explaining why viability was lost abruptly. Therefore, milder conditions were applied in order to observe a gradual loss of viability. In the new protocol, neurons were first exposed for 40 min to 250 µM XAN in the presence of various concentrations of XAO (0–20 mU/mL), and then readily incubated in fresh culture medium in the presence of AlamarBlue for 7 h. If there was residual amount of XAO left in the fresh medium, it increased mortality but in a manner proportional to the initial concentration of the enzyme. With the new protocol, the loss of viability caused by XA/XAO was indeed gradual and depended on the concentration of XAO in the solution (FIG. 4). Interestingly, 0.5×TRIAD was sufficient to provide almost complete protection in those conditions.

3.3 Neuroprotection Afforded by TRIAD Against Oxidative Stress Induced by $H_2O_2$ FIG. 5 shows that P19 neurons died in a concentration dependent manner when exposed to hydrogen peroxide. The $LD_{50}$ value was 0.3 mM hydrogen peroxide. TRIAD protected cells against death caused by $H_2O_2$ and a complete protection was achieved with 1× concentration of the antioxidant mix. TRIAD 3× and 5× also provided complete protection (not shown). When assayed at 0.5× suboptimal concentration of TRIAD, fatty acids or vitamin E alone did not provide protection against oxidative stress caused by hydrogen peroxide (not shown). Combination of these agents was protective up to 0.5 mM $H_2O_2$ but fell off rapidly at higher concentrations of the prooxidant (FIG. 6).

In contrast, pyruvate provided a substantial and stable protection up to 10 mM $H_2O_2$ (FIG. 6). Comparison of the protection separately provided by 0.5× pyruvate and 0.5× TRIAD shows that 0.5×TRIAD was more efficient by about 2-fold (FIG. 6), indicating that fatty acids and vitamin E increased the protective action of pyruvate in a synergistic manner.

3.4 Neuroprotection Afforded by TRIAD Against Oxidative Stress Induced by $H_2O_2$ in the Presence of Iron Addition of $Fe^{2+}$ to generate hydroxyl radicals was slightly more deleterious to neurons than hydrogen peroxide alone. As an example, 1 mM $H_2O_2$ caused approximately 70% cell mortality (FIG. 5) whereas the same concentration of peroxide in the presence of iron caused more than 80% cell mortality (FIG. 7). This is in agreement with the relative oxidant power of each system (FIG. 1 and section 3.1). Increased stress required 3×TRIAD instead of 1× to provide complete neuroprotection (FIG. 7). Pyruvate contributed for most of TRIAD protective effect in this prooxidant system (FIG. 8).

3.5 In vitro Antioxidant Capacity of TRIAD with Peroxide-based Prooxidant Systems Used with Cultured Neurons Antioxidant capacity of TRIAD and of its components were evaluated in vitro by following oxidation of DPD by the two peroxide-based prooxidant systems. FIGS. 9 and 10 show that optimal antioxidant concentrations of TRIAD for peroxide systems are smaller in vitro than in cell culture situations. Indeed, 0.5× and 1×TRIAD respectively abolished DPD oxidation (FIG. 9) and neuron mortality (FIG. 5) induced by oxidative stress in the $H_2O_2$ system, and the counterpart values were 1× (FIG. 7) and 3× (FIG. 10) for the $H_2O_2/Fe^{2+}$ system. These observations suggest that even low levels of oxidative stress could exert irreversible detrimental effects on cells, requiring higher concentrations of TRIAD to be prevented.

Results of DPD oxidation measurement show that there are resemblance and also differences regarding the relative protection afforded by each component of TRIAD in vitro, compared to cell culture situations, giving clues on the possible mechanism of action of TRIAD. Differences were obvious with the $H_2O_2$ system. In cultured neurons, pyruvate mostly (60%) contributed to the neuroprotective action of TRIAD against $H_2O_2$-induced injury whereas fatty acids and vitamin E did not by themselves provide much protection to cells (less than 10% for peroxide concentration higher than 1 mM) although they increased pyruvate action synergistically (section 3.3 and FIG. 6). In contrast, in vitro, fatty acids+vitamin E completely inhibited the oxidation of DPD by $H_2O_2$ while pyruvate also provided a substantial although not total antioxidant effect (FIG. 11). Discrepancy between cultured cells and in vitro situations could be explained by the presence or absence of a cell membrane barrier which distinguishes inside and outside protection. In vitro, fatty acids+vitamin E combination and pyruvate can separately inhibit DPD oxidation by $H_2O_2$ because they are all in the same compartment. In contrast, there are at least two compartments in cell cultures (inside and outside cells). Because pyruvate can be uptaken by neurons, it can protect them from both exterior and interior damages induced by an excess of $H_2O_2$ which is known to diffuse easily through cell membranes. Fatty acids (including lecithin present in egg yolk) and vitamin E which do not pass easily through membranes during the 30 min of treatment, could not afford important intracellular protection but rather helped pyruvate by providing extracellular defense. Fatty acids+vitamin E combination were only as powerful as pyruvate to inhibit DPD oxidation when iron was added to hydrogen peroxide (FIG. 12). It is possible that this combination lost part of its antioxidant properties because egg yolk fatty acids were deteriorated by iron-catalyzed formation of hydroxyl radicals which are known to initiate lipid peroxidation (Gutteridge, 1994; Chan, 1996). Neurons would thus count more on pyruvate for their protection in the $H_2O_2/Fe^{+2}$ than in the $H_2O_2$ system. Unfortunately, the XA/XAO system could not oxidize DPD by itself. Therefore direct comparison between this system and the peroxide-based systems cannot readily be made.

4. Discussion

This study showed that TRIAD has an antioxidant capacity in vitro and a protective action on cultured P19 neurons exposed to oxidative stress. The results are summarized in Table 1 below and indicate that association of pyruvate, vitamin E and fatty acids can protect cells against extracellular and intracellular oxidative damages, by different mechanisms. Since oxidative damage in vivo can be caused by extracellular or intracellular (or both) ROS sources, association of the three components of TRIAD appears very useful.

TABLE I

| | Minimal concentration of TRIAD (X-fold) for complete antioxidant protection. | | |
|---|---|---|---|
| | Prooxidant system | | |
| Model | XA/XAO | $H_2O_2$ | $H_2O_2/Fe^{2+}$ |
| Neurons (Vit.E) | ≈0.5× (Pyruvate > F.A. + Vit.E) ↑ or ↑↑ | 1× (Pyruvate > F.A. + Vit.E) ↑↑ or ↑↑↑ | 3× (Pyruvate > F.A. + Vit.E) ↑ or ↑↑ |

TABLE I-continued

Minimal concentration of TRIAD (X-fold) for complete antioxidant protection.

| | Prooxidant system | | |
|---|---|---|---|
| Model | XA/XAO | $H_2O_2$ | $H_2O_2/Fe^{2+}$ |
| In vitro | Not determined* | 0.5×<br>(F.A. + Vit.E ><br>Pyruvate)<br>↑ | 1×<br>(Pyruvate ≅ F.A. +<br>Vit.E)<br>↑↑ |

The results are presented for cultured P19 neurons and their in vitro counterpart (i.e. prooxidant conditions tested on DPD, in absence of cells). The relative contribution of pyruvate and of F.A. + Vit.E is given between parentheses. The accompanying arrows indicate that pyruvate action was apparently increased in less than additive (↑), additive (↑↑) or synergistic (↑↑↑) manner by F.A. + Vit.E.
*not determined because the prooxidant system cannot directly oxidize DPD.
F.A.: fatty acids; Vit.E: vitamin E.

Although not shown in this study, the Inventors have demonstrated that TRIAD protected hearts against oxidative stress generated via several important ROS ($.O_2^-$, $H_2O_2$ and .OH), physiologically produced in ischemia-reperfusion conditions. Smaller concentrations of TRIAD was needed to protect isolated heart from ischemia-reperfusion induced damages than to protect isolated neurons. There are several explanations to this difference. First, concentrations of ROS used in this study with neurons were high and likely more important than those encountered naturally. In addition, ROS produced exogenously have conceivably an easier access to cells grown as monolayers than to cells tightly organized within an organ, and organ being formed of different types of cells, it likely possesses a larger spectrum of antioxidant defenses than have monotypic cells in cultures. However, 1× and 3× were very effective concentrations of TRIAD in cultured neurons. In peroxide-based prooxidant systems, concentration dependency of the protective effect of TRIAD in cultured cells matched that of its antioxidant capacity in vitro. However, higher concentrations than those predicted from in vitro analyses were systematically needed with neurons. These results suggest that cellular damages can accumulate before TRIAD entirely exerts its protective action and/or that cellular metabolism can trigger ROS transformation from one type to a more reactive one.

Pyruvate was the most important component of TRIAD with cultured neurons, accounting for 60 to 90% of the protective action of TRIAD. Fatty acids and vitamin E by themselves did not provide much protection but they increased the protective effect of TRIAD, most often in an additive but sometimes in a synergistic manner. Pyruvate is considered as an important scavenger of $H_2O_2$ and compared to the other agents of TRIAD, provides important intracellular neuroprotection due to the capacity of neurons to import pyruvate from extracellular sources. As an exception to the important contribution of pyruvate, antioxidant capacities of TRIAD in vitro with $H_2O_2$ prooxidant system was mainly contributed by fatty acids and vitamin E. Addition of $Fe^{+2}$ to $H_2O_2$ diminished the antioxidant power of fatty acids+vitamin E in vitro, an effect which could be related to a possible peroxidation of egg yolk lipids by newly formed hydroxyl radicals.

The Applicant is aware of the apparent contradiction between the results obtained with cultured neurons (FIG. 6, where pyruvate is the major protector) and those obtained with DPD (FIG. 11, where pyruvate is not the major protector) for $H_2O_2$ system, as discussed in the precedent paragraph. A possible explanation for this observation is the existence of at least two compartments in the cell situation (intracellular and extracellular compartments) compared to only one compartment in the test tube assay.

In vitro, either pyruvate alone or the combination of vitamin E+fatty acids is in concentration sufficient to decrease or prevent DPD oxidation by hydrogen peroxide (FIG. 11). However, damages caused to cells by hydrogen peroxide are intra- as well as extracellular, since this ROS can pass through cell membrane. In vivo, pyruvate would provide intracellular protection because it is uptaken by cells, while vitamin E and fatty acids which do not pass cell membranes provide extracellular protection only. One could imagine that if cells are permeabilized, then vitamin E+fatty acids and pyruvate would perhaps provide an overall protection resembling that seen in vitro. However, the formulation of TRIAD tested, has the advantage of both extracellular (membrane) and intracellular effects.

The neuroprotective action of TRIAD is likely related to its three components. Pyruvate, able to enter the cell, will enhance intracellular defense, while vitamin E and fatty acids will improve membrane functionality, eventually limiting the leakage of cellular $Fe^{2+}$ ion (easily generated by reduction of $Fe^{3+} \rightarrow Fe^{2+}$, induced by superoxide anion which is a reductive agent), preventing thus the production of hydroxyl radical (.OH) via the Fenton and Haber-Weiss reactions, Fenton reaction: $Fe^{2+} + H_2O_2 \rightarrow Fe^{3+} + .OH + OH^-$ Haber-Weiss reaction: $Fe^{3+} + .O_2^- \rightarrow Fe^{2+} + O_2$ Mechanisms of iron involvement are not fully elucidated, but there is a growing consensus that oxidative issue damage is related to non-heme cellular iron mobilized from cytosolic metal-containing sites: e.g. ferritin stores within cells.

In this work, the protective effect of TRIAD was studied during co-exposure of neurons to both prooxidant conditions and TRIAD. In a therapeutic point of view, this antioxidant TRIAD mix could conceivably be also used to prevent damages caused to tissues by acute or chronic exposure to oxidative stress or to recover from such injuries. In this aspect, the potential of egg yolk to serve as a source of fatty acids to repair membrane damages and that of pyruvate to serve as fuel for cells could confer important neurotrophic properties to TRIAD and extent application of TRIAD to neurodegenerative diseases. This is particularly relevant since oxidative stress is considered as an etiologic or at least an aggravating factor in several of these diseases. TRIAD thus has a high therapeutic potential in preventive or reparative strategies.

5. Conclusive Remarks

This study shows that TRIAD has an antioxidant neuroprotective action on cultured P19 neurons exposed to oxidative stress. Optimal concentrations vary with the type and prooxidant power of ROS generating systems. Pyruvate is a major contributor of antioxidant properties of TRIAD ex vivo (heart, not shown) and in neuronal cultures, especially when TRIAD is administered just prior induction of an oxidative stress and remains present for short time of treatment (30–40 min for neurons). The contribution of vitamin E and egg yolk fatty acids may appear even more important in antioxidant defense when TRIAD is administered for longer periods (before, during and after oxidative stress).

This study also yields in the development of an essential concept which comprises two aspects:

i) combinations of antioxidants having different mechanism of action provide higher protection to oxidative stress than any single antioxidant; and ii) synergistic protection is a "latent" property of antioxidant combinations and does not necessarily manifest itself in all prooxidant conditions.

Aspect ii) is best illustrated by the results of FIG. 6 which showed that while pyruvate and vitamin E+fatty acids each provides half of the protective effect of TRIAD at low hydrogen peroxide concentrations, at higher concentrations of the prooxidant, TRIAD remained almost as protective even though vitamin E+fatty acids were no longer active by themselves. Synergistic neuroprotection was thus seen under more pronounced oxidative stress conditions.

Finally, although the term "TRIAD" used herein refers to a composition comprising sodium pyruvate, vitamin E and egg yolk fatty acids, a person skilled in the art will understand that the compositions of the present invention are not restricted to these sole specific components as explained previously in the first part of the section "DETAILED DESCRIPTION OF THE INVENTION".

6. References

Throughout this paper, reference is made to a number of articles of scientific literature which are listed below:

Anonymous (1985) DPD calorimetric method. Standard methods for the examination of water and wastewater. New-York, *APHA, AWWA, WPCF,* 16$^{th}$ ed., 306–309.
Chahine, R., Mateescu, M. A., Roger, S., Yamaguchi, N., De Champlain, J. and Nadeau, R. (1991) Can. J. Physiol. Pharmacol. 69, 1459–1464.
Chan, P. (1996) Stroke 27, 1124–1129.
Cini, M., Fariello, R. G., Bianchetti, A. and Moretti, A. (1994) Neurochem. Res. 19, 283–288.
Desagher, S., Glowinski, J. and Premont J. (1996) J. Neurosci. 16, 2553–2562.
Finley, M. F. A., Kulkarni, N. and Hutter, J. E. (1996) J. Neurosci. 16, 1056–1065.
Gokhale, M. S., Lin, J. R. and Yager, J. D. (1997) Toxicol. in Vitro 11, 753–759.
Gutteridge, J. M. C. (1994) Annu. N.Y. Acad. Sci. 738, 201–213.
LeBel, C.P. and Bondy, S. C. (1991) Neurotox. Teratol. 13, 341–346.
Jeannotte, R., Paquin, J., Petit-Turcotte, C. and Day, R. (1997) DNA Cell Biol. 16, 1175–1187.
Maiese, K. (1998) Clin. Neuropharmacol. 1, 1–17.
Martin, A. (1994) U.S. Pat. No. 5,926,370.
Martin, A. (1996) Dermatol. Surg. 22, 156–160.
McBurney, M. W. (1993) Int. J. Dev. Biol. 37, 135–140.
Parnas, D. and Linial, M. (1997) Molec. J. Neurosci. 8, 115–130
Sheridan, J., Kern, E., Martin, A. and Booth, A. (1997) Antiviral Res. 36, 157–166.
Takemura, G., Onodera, T. and Ashraf, M. (1994) J. Mol. Cell Cardiol. 26, 41–454.
Yao, M., Bain, M. Y. G. and Gottlieb, D. I. (1995) J. Neurosci. Res. 41, 792–804.

Of course, numerous modifications and improvements could be made to the embodiments that have been disclosed herein above. These modifications and improvements should, therefore, be considered a part of the invention.

What is claimed is:

1. A method for treating a neuronal oxidative stress related condition comprising the administration to a patient in need thereof of a therapeutically effective amount of an antioxidative composition comprising pyruvate, at least one antioxidant and at least one lipid.

2. The method of claim 1, wherein said pyruvate, antioxidant and lipid are present in said composition in an amount that have a synergistic protective effect on neuronal cells.

3. The method of claim 1, wherein said at least one lipid consists of at least one fatty acid selected from the group consisting of monoglycerides, diglycerides, triglycerides, free fatty acids, and mixtures thereof.

4. The method of claim 3, characterized in that said at least one fatty acid consists of a mixture of saturated and unsaturated fatty acids.

5. The method of claim 4, characterized in that said fatty acids are present in an amount varying from about 0.001% v/v to about 1% v/v, by weight of the neuroprotective composition.

6. The method of claim 1, wherein pyruvate is selected from the group consisting of pyruvic acid, pharmaceutically acceptable salts of pyruvic acid, prodrugs of pyruvic acid, and mixtures thereof.

7. The method of claim 1, wherein pyruvate is present in said composition in an amount varying from about 0.1 mM to about 100 mM.

8. The method of claim 1, wherein said at least one antioxidant is selected from lipid-soluble antioxidants.

9. The method of claim 1, wherein said at least one antioxidant is selected from the group consisting of Vitamin A, carotene, Vitamin E, pharmaceutically acceptable salts thereof, and mixtures thereof.

10. The method of claim 1, wherein said at least one antioxidant is selected from the group consisting of Vitamin E, Vitamin E acetate and analogues of Vitamin E.

11. The method of claim 1, wherein said at least one antioxidant is present in the composition in an amount varying from about 0.01 unit/ml to about 10 unit/ml of the composition.

12. The method of claim 1, wherein the composition further comprises an agent selected from the group consisting of metal chelators, metal scavengers, proteinic metal chelators, proteinic scavengers, preserving agents, solubilizing agents, stabilizing agents, wetting agents, emulsifiers, sweeteners, colorants, odorants, salts, buffers and coating agents.

13. The method of claim 1, for the treatment of brain trauma, neurodegenerative disease(s), poisoning of neuronal cells, and for the diminution of drugs side effects.

14. A method for treating a neuronal oxidative stress related condition comprising:
administrating to a patient in need thereof of a therapeutically effective amount of an antioxidative composition comprising pyruvate and at least one antioxidant; and
providing into blood circulation of said patient at least one lipid having a synergistic therapeutic effect on neuronal cells in combination with said antioxidative composition.

15. The method of claim 14, wherein said at least one lipid is provided to said patient by increasing its lipidic blood level ratio through its diet.

16. The method of claim 14, wherein said neuronal oxidative stress related condition is a brain trauma, amyotrophic lateral sclerosis, a neurodegenerative disease, neuronal cells poisoning, side effects caused by a drug or handling of a neuronal graft.

17. A method for the treatment of oxidative stress in neuronal cells, comprising contacting said cells with a therapeutically effective amount of an antioxidative composition comprising pyruvate, at least one antioxidant and at least one lipid.

18. The method of claim 17, for protecting neuronal cells in vitro, in vivo and ex vivo against an oxidative stress related condition.

19. The method of claim 17, for the treatment of brain trauma, neurodegenerative disease(s), poisoning of neuronal cells, for the diminution of drugs side effects and for the preservation of neuronal grafts.

* * * * *